US012622779B2

(12) United States Patent
Colavito et al.

(10) Patent No.: US 12,622,779 B2
(45) Date of Patent: May 12, 2026

(54) VALVED CONDUIT WITH EXPANDABLE FRAME

(71) Applicant: Edwards Lifesciences Corporation, Irvine, CA (US)

(72) Inventors: Kyle W. Colavito, Flagstaff, AZ (US); Michael J. Shepard, Flagstaff, AZ (US)

(73) Assignee: Edwards Lifesciences Corporation, Irvine, CA (US)

( * ) Notice: Subject to any disclaimer, the term of this patent is extended or adjusted under 35 U.S.C. 154(b) by 1132 days.

(21) Appl. No.: 17/609,176

(22) PCT Filed: May 6, 2020

(86) PCT No.: PCT/US2020/031597

§ 371 (c)(1),
(2) Date: Nov. 5, 2021

(87) PCT Pub. No.: WO2020/227359

PCT Pub. Date: Nov. 12, 2020

(65) Prior Publication Data

US 2022/0226109 A1 Jul. 21, 2022

Related U.S. Application Data

(60) Provisional application No. 62/843,911, filed on May 6, 2019.

(51) Int. Cl.
*A61F 2/24* (2006.01)

(52) U.S. Cl.
CPC .... *A61F 2/2418* (2013.01); *A61F 2230/0013* (2013.01); *A61F 2250/001* (2013.01); *A61F 2250/0082* (2013.01)

(58) Field of Classification Search
CPC ..................................................... A61F 2/2418
See application file for complete search history.

(56) References Cited

U.S. PATENT DOCUMENTS

| | | | |
|---|---|---|---|
| 8,961,593 B2 | 2/2015 | Bonhoeffer | |
| 9,364,322 B2 | 6/2016 | Conklin | |
| 9,636,219 B2 | 5/2017 | Keidar | |
| 9,675,453 B2 * | 6/2017 | Guttenberg | ........... A61F 2/2418 |
| 10,052,200 B2 | 8/2018 | Chung | |
| 11,071,626 B2 * | 7/2021 | Colavito | ............... A61F 2/2412 |
| 11,083,574 B2 * | 8/2021 | Sievers | ................ A61F 2/2418 |

FOREIGN PATENT DOCUMENTS

| | | |
|---|---|---|
| CN | 108601653 A | 9/2018 |
| WO | WO-2009/108355 | 9/2009 |
| WO | WO-2012018779 A2 | 2/2012 |
| WO | WO2012018779 A3 | 5/2012 |
| WO | WO-2015/014960 | 2/2015 |
| WO | WO-2019/178581 | 9/2019 |

OTHER PUBLICATIONS

International Search Report for PCT/US2020/031597 mailed Jul. 1, 2020, 5 pages.

* cited by examiner

*Primary Examiner* — Brian A Dukert
(74) *Attorney, Agent, or Firm* — Klarquist Sparkman LLP

(57) ABSTRACT

Various aspects of the present disclosure are directed toward apparatuses, systems, and methods that include a valved conduit. The valved conduit may include a frame element arranged within the conduit and one or more expansion elements configured to spread apart to radially expand the frame.

14 Claims, 4 Drawing Sheets

VALVED CONDUIT WITH EXPANDABLE FRAME

CROSS-REFERENCE TO RELATED APPLICATION

This application is a 35 U.S.C. 371 Application of International Application PCT/US2020/031597, filed May 6, 2020, which claims the benefit of Provisional Application No. 62/843,911, filed May 6, 2019, which are incorporated herein by reference in their entireties for all purposes.

FIELD

The present disclosure relates generally to prosthetic valves and more specifically to apparatuses, systems, and methods that include conduits having an expandable frame therein.

BACKGROUND

Bioprosthetic heart valves have been developed that attempt to mimic the function and performance of a native valve. Flexible leaflets may be mechanically coupled to a relatively rigid frame that supports the leaflets and provides dimensional stability when implanted. Although bioprosthetic heart valves can provide excellent hemodynamic and biomechanical performance in the short term, they are prone to calcification and cusp tears, among other failure modes, requiring reoperation and replacement.

In certain instances, leaflets may be arranged within a conduit, such as a pulmonary valve conduit. However, various situations arise in which the requisite diametric profile of a valved conduit changes from one point in time to another. For example, in pediatric applications, a valve portion of the valved conduit with a first, smaller inner diameter (i.e., the inner flow diameter) may be appropriate, but following growth of the patient, a larger inner diameter for the prosthetic valve is desirable. The removal of an existing valve and/or implantation of another valve with a larger flow diameter may give rise to various complications and concomitant risks.

SUMMARY

According to one example ("Example 1"), a valved conduit includes a conduit having an interior surface and an exterior surface; and a frame element arranged within the conduit and having commissure posts arranged about the frame element, the frame element having a first diameter in a first configuration and configured to support a valve structure having leaflets configured to open to permit flow and close to occlude a conduit lumen and prevent flow in response to differential fluid pressure and to expand to a second, larger diameter in a second configuration in response to a force applied to an interior portion of the frame element; and one or more expansion elements arranged between or adjacent to the commissure posts and configured to spread apart to radially expand the frame element in transitioning between the first configuration and the second configuration.

According to another example ("Example 2"), further to the valved conduit of Example 1, the frame element is configured to house a second valve structure therein in the second configuration.

According to another example ("Example 3"), further to the valved conduit of any one of Examples 1-2, the frame element includes a first circular rim and a second circular rim connected by the commissure posts, and the one or more expansion elements form portions of at least one of the first circular rim and the second circular rim.

According to another example ("Example 4"), further to the valved conduit of Example 3, the one or more expansion elements are arranged with one of the first circular rim and the second circular rim and extend toward another of the first circular rim and the second circular rim.

According to another example ("Example 5"), further to the valved conduit of Example 4, the one or more expansion elements include a first linear portion, a second linear portion, and a curved portion.

According to another example ("Example 6"), further to the valved conduit of Example 5, the first linear portion and the second linear portion extend substantially parallel with a longitudinal axis of the frame element in the first configuration and are configured to angle relative to the longitudinal axis of the frame element in the second configuration.

According to another example ("Example 7"), further to the valved conduit of any one of Examples 1-6, the one or more expansion elements are arranged between the commissure posts.

According to another example ("Example 8"), further to the valved conduit of any one of Examples 1-7, the one or more expansion elements are arranged adjacent to the commissure posts.

According to another example ("Example 9"), further to the valved conduit of any one of Examples 1-8, the one or more expansion elements are arranged between portions of the commissure posts.

According to another example ("Example 10"), further to the valved conduit of any one of Examples 1-9, the frame element includes a plurality commissure posts and the one or more expansion elements includes a plurality of expansion elements arranged between portions of each of the commissure posts.

According to another example ("Example 11"), further to the valved conduit of Example 10, the valved conduit also includes a plurality of additional expansion elements arranged between the commissure posts.

According to another example ("Example 12"), further to the valved conduit of any one of Examples 1-11, the one or more expansion elements are configured to increase a diameter of the frame element.

According to one example ("Example 13"), an expandable prosthetic device includes a valve structure; and a frame element configured to support the valve structure in a first configuration and including one or more expansion elements configured to radially expand the frame element to a second configuration having a diameter larger than a diameter of the frame element in the first configuration to accommodate a secondary valve structure in the second configuration and maintain a continuous outer perimeter.

According to another example ("Example 14"), further to the expandable prosthetic device of Example 13, the frame element includes a first circular rim and a second circular rim and one or more expansion elements form portions of at least one of the first circular rim and the second circular rim.

According to another example ("Example 15"), further to the expandable prosthetic device of Example 14, the one or more expansion elements include a first linear portion and a second linear portion, and the first linear portion and the second linear portion extend substantially parallel with a longitudinal axis of the frame element in the first configuration and are configured to angle relative to the longitudinal axis of the frame element in the second configuration.

According to another example ("Example 16"), further to the expandable prosthetic device of Example 13, the device also includes a conduit, and the frame element is arranged within the conduit.

According to one example ("Example 17"), a method of repairing or replacing an aortic valve or a pulmonary valve of a patient includes arranging a valved conduit at a target location within the patient, the valved conduit within including a valve structure, a frame element configured to support a valve structure includes leaflets configured to open to permit flow and close to occlude a conduit lumen and prevent flow in response to differential fluid pressure in a first configuration and including one or more expansion elements configured to radially expand the frame element; applying a force interior to the frame element to radially expand the frame element to a second configuration having a larger diameter than the first configuration while maintaining a continuous outer perimeter of the frame element; and arranging a secondary valve structure within the expanded frame element.

According to another example ("Example 18"), further to the method of Example 17, arranging the valved conduit includes deploying the valved conduit to replace the pulmonary valve of the patient.

According to another example ("Example 19"), further to the method of Example 17, the frame element includes a first circular rim and a second circular rim and one or more expansion elements form portions of at least one of the first circular rim and the second circular rim and one or more expansion elements include a first linear portion and a second linear portion, and the first linear portion and the second linear portion extend substantially parallel with a longitudinal axis of the frame element in the first configuration and are configured to angle relative to the longitudinal axis of the frame element in the second configuration.

According to another example ("Example 20"), further to the method of Example 19, the first linear portion and the second linear portion extend substantially parallel with a longitudinal axis of the frame element in the first configuration and are configured to angle relative to the longitudinal axis of the frame element in the second configuration.

According to one example ("Example 21"), a valved conduit for housing a first valve structure and allowing expansion for housing a second valve structure including a conduit having an interior surface and an exterior surface; and a frame element arranged within the conduit including a first diameter in a first configuration and configured to support the first valve structure having leaflets configured to open to permit flow and close to occlude a conduit lumen and prevent flow in response to differential fluid pressure, the frame element having: a first circular rim, a second circular rim, commissure posts arranged about the frame element and connecting the first circular rim and the second circular rim, upper expansion elements arranged between or adjacent to the commissure posts along the first circular rim, and lower expansion elements arranged between or adjacent to the commissure posts along the second circular rim, at least one of the upper expansion elements and the lower expansion elements being configured to spread apart to radially expand the frame element in transitioning between the first configuration and a second, larger diameter in a second configuration to support the second valve structure having leaflets in response to a force applied to an interior portion of the frame element.

According to another example ("Example 22"), the valved conduit of Example 21, the frame element is configured to deform to maintain gaps between the leaflets of the second valve structure.

According to another example ("Example 23"), the valved conduit of Example 21, the upper expansion elements and the lower expansion elements configured to hold the frame element in the second configuration at a diameter intended by the interior radial force.

According to another example ("Example 24"), the valved conduit of Example 21, the upper expansion elements and the lower expansion elements are configured to expand in a sloped manner to expand the frame element linearly.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Definitions and Terminology

Figure 1B:
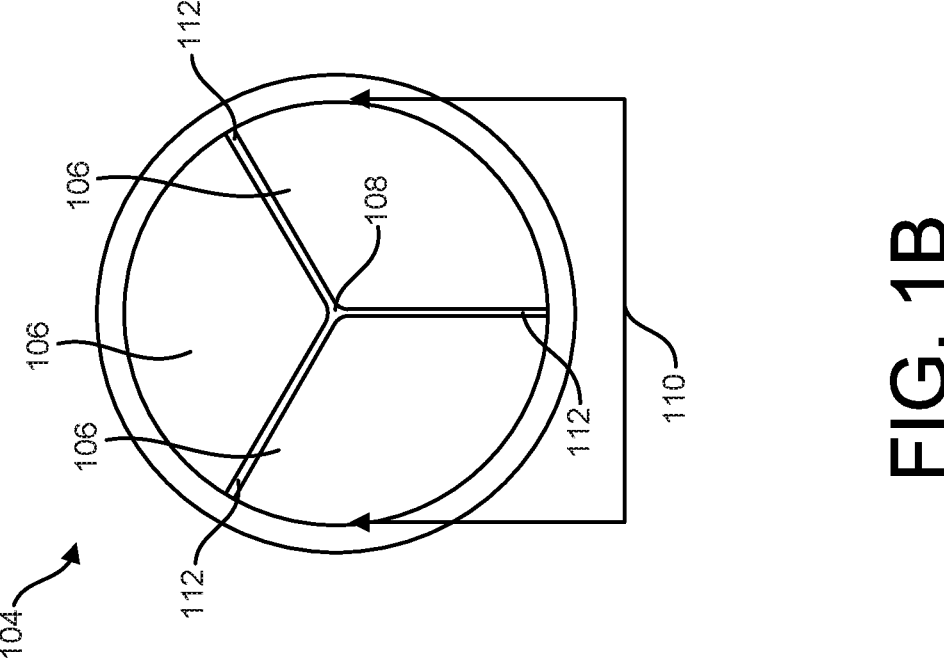
FIG. 1B illustrates an interior downstream view of a valve structure in a closed configuration, as shown in FIG. 1A.

This disclosure is not meant to be read in a restrictive manner. For example, the terminology used in the application should be read broadly in the context of the meaning those in the field would attribute such terminology.

With respect to terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error, differences in measurement and/or manufacturing equipment calibration, human error in reading and/or setting measurements, minor adjustments made to optimize performance and/or structural parameters in view of differences in measurements associated with other components, particular implementation scenarios, imprecise adjustment and/or manipulation of objects by a person or machine, and/or the like, for example. In the event it is determined that individuals having ordinary skill in the relevant arts would not readily ascertain values for such reasonably small differences, the terms "about" and "approximately" can be understood to mean plus or minus 10% of the stated value.

Description of Various Embodiments

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valved conduits. However, embodiments within the scope of this disclosure can be applied toward any valved conduit, valve structure, or mechanism of similar structure and/or function. Furthermore, embodiments within the scope of this disclosure can be applied in non-cardiac applications.

Various aspects of the present disclosure are directed toward apparatuses, systems, and methods for a conduit having a valve structure operable as a prosthetic valve that can be used, such as, but not limited to, replace a pulmonary valve and a portion of the corresponding pulmonary artery. The valve structure may include one or more leaflets operable as a one-way valve with the conduit defining a conduit lumen. The leaflet(s) open to permit flow and close to occlude the conduit lumen and prevent flow in response to differential fluid pressure. In addition, the conduit may include a frame element that supports the valve structure. In certain instances, the patient having the conduit may grow out of the conduit such that the valve structure is no longer functional or is not functioning as desired. As discussed in further detail below, the frame element may be configured to expand to allow for a second valve structure to be installed within the frame element/valve structure of the conduit. The second valve structure may be a prosthetic valve that can be deployed in place of the previously deployed valve structure (within the conduit).

Embodiments herein include various apparatuses, systems, and methods for a conduit having a valve structure operable as a prosthetic valve that can be used, such as, but not limited to, replace an aortic valve and a portion of the aorta, such as the ascending aorta. The conduit is operable to be surgically coupled to the left atrium at a conduit proximal end and to a portion of the ascending aorta as a conduit distal end. In other embodiments, the conduit is also operable for the surgical attachment of one or more coronary arteries thereto to establish blood flow thereto.

Figure 1A:
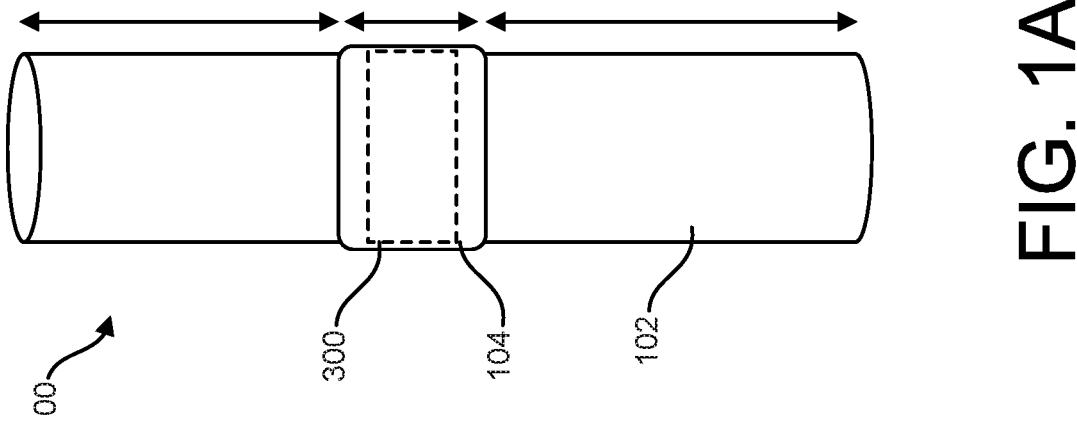
FIG. 1A is an illustration of an example valved conduit, in accordance with an embodiment.

FIG. 1A is an illustration of an example valved conduit 100, in accordance with an embodiment. The valved conduit 100 includes a conduit 102 with a valve structure 104 arranged within the conduit 102. The conduit 102 may include an upstream end and a downstream end such that the valve structure 104 allows flow in one direction.

The valved conduit 100 may be used, in a non-limiting example, to replace an aortic valve and at least a portion of the ascending aorta. In one non-limiting example, the valved conduit 100 may be indicated for the correction or reconstruction of the aortic root and aortic valve, i.e., aortic root replacement, in pediatric patients. The valved conduit 100 may also be indicated for the replacement of previously implanted homografts or valved conduits that have become dysfunctional or insufficient.

The valved conduit 100 may be used, in a non-limiting example, as a shunt for connecting of the right ventricle to the pulmonary artery following a Norwood operation, as frequently performed for the treatment of hypoplastic left heart syndrome. In one non-limiting example, the valved conduit 100 may be indicated for the correction or reconstruction of the right ventricle outflow tract (RVOT) in pediatric patients. Such reconstruction may be indicated for congenital heart disorders such as tetralogy of Fallot, Truncus Arterious, Dextro-Transposition of the Great Arteries, Pulmonary Atresia of Intact Ventricular Septum, or Aortic Valvular Disease. The valved conduit 100 may also be indicated for the replacement of previously implanted homografts or valved conduits that have become dysfunctional or insufficient. In addition, the valved conduit 100 may have applications in treating a wider range of heart disorders, including other areas of the heart. Generally, the term "distal" is used in the disclosure to refer to the outflow end (distal end) or outflow direction of a valved conduit 100, and in turn the term "proximal" is used to refer to the inflow end of a valved conduit 100, or a direction opposite the direction of primary flow through the valved conduit 100.

Figure 2:
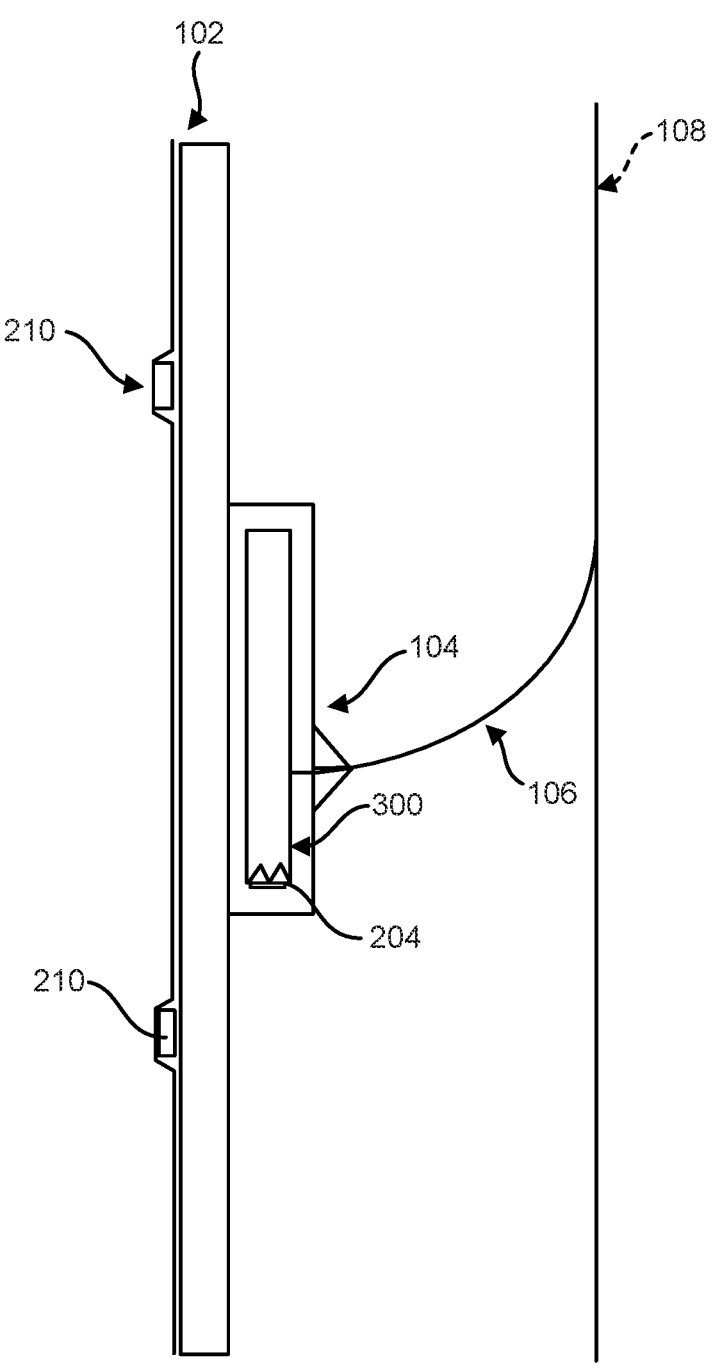
FIG. 2 is a cross-sectional illustration of a conduit, frame element and valve structure, in accordance with an embodiment.

As shown in FIG. 1A and in further detail in FIG. 2, the valved conduit 100 may include a frame element 300. The frame element 300 may be configured to support the valve structure 104 and leaflets 106. The valve structure 104 may be formed of silicone or another flexible polymer that is applied to an exterior surface or portion (e.g., outside diameter) of a frame element 300. In certain instances, the conduit 100 is formed of a graft material and the frame element 300 is the sole supporting structure arranged with the conduit 100. The conduit 100, for example, may be free of stent or stent like features with the exception of the frame element 300.

FIG. 1B illustrates an interior downstream view of a valve structure 104 in a closed configuration, as shown in FIG. 1A. The valve structure 104 includes leaflets 106 that extend into an interior of the conduit 102. Although three leaflets 106 are shown in FIG. 1B, the valve structure 104 may include one, two, three four, five, six, seven, eight or greater number of leaflets 106. As shown in FIG. 1B, the leaflets 106 close toward a center 108 of the conduit 102 in the closed configuration. As shown in FIG. 1B, gaps 112 exist between each of the leaflets 106. The gaps 112 allow backflow through the conduit 102. The backflow lessens the opportunity for blood to stagnate behind the leaflet 106, which can lead to thrombus formation. The gaps 112 are sized such that leakage resulting from the backflow is minimal and does not otherwise increase strain on the patient's heart to pump blood through the conduit 102. In an open configuration, blood may flow through the valve structure 104 with the leaflets 106 being forced toward an interior surface 110 of the conduit 102. The leaflets 106 may be coupled to the frame element 300 as described in FIG. 2. The leaflets 106 are configured open to permit flow and close to occlude the conduit lumen and prevent flow in response to differential fluid pressure.

FIG. 2 is a cross-sectional illustration of a conduit 102, frame element 300 and valve structure 104, in accordance with an embodiment. The valve structure 104, which may include the frame element 300, is arranged within the conduit 102 such that the leaflets 106 extend into the conduit 102 and toward the center 108 of the conduit 102. The valve structure 104 may be coupled or adhered the frame element 300 and/or the conduit 102.

In certain instances, the conduit 102 may include one or more radiopaque markers 210 to assist in visualizing a location of the frame element 300 within the conduit 102 post-procedure under fluoroscopic visualization. The one or more radiopaque markers 210 can be arranged adjacent to the frame element 300. In other instances, the conduit 102 does not include any radiopaque markets 210 as the frame element 300 may be radiopaque.

The frame element 300, as discussed in further detail below, is configured to support the valve structure 104 and leaflets 106 in a first configuration as shown in FIG. 2. The frame element 300 may include one or more expansion elements 204 that are configured to spread apart to radially expand the frame element 300 to a second configuration having a diameter larger than a diameter of the frame element 300 in the first configuration. The one or more expansion elements 204 are configured to expand a diameter of the frame element 300 such that a secondary valve structure may be arranged within the frame element 300 in the second configuration.

Figures 3A, 3B:
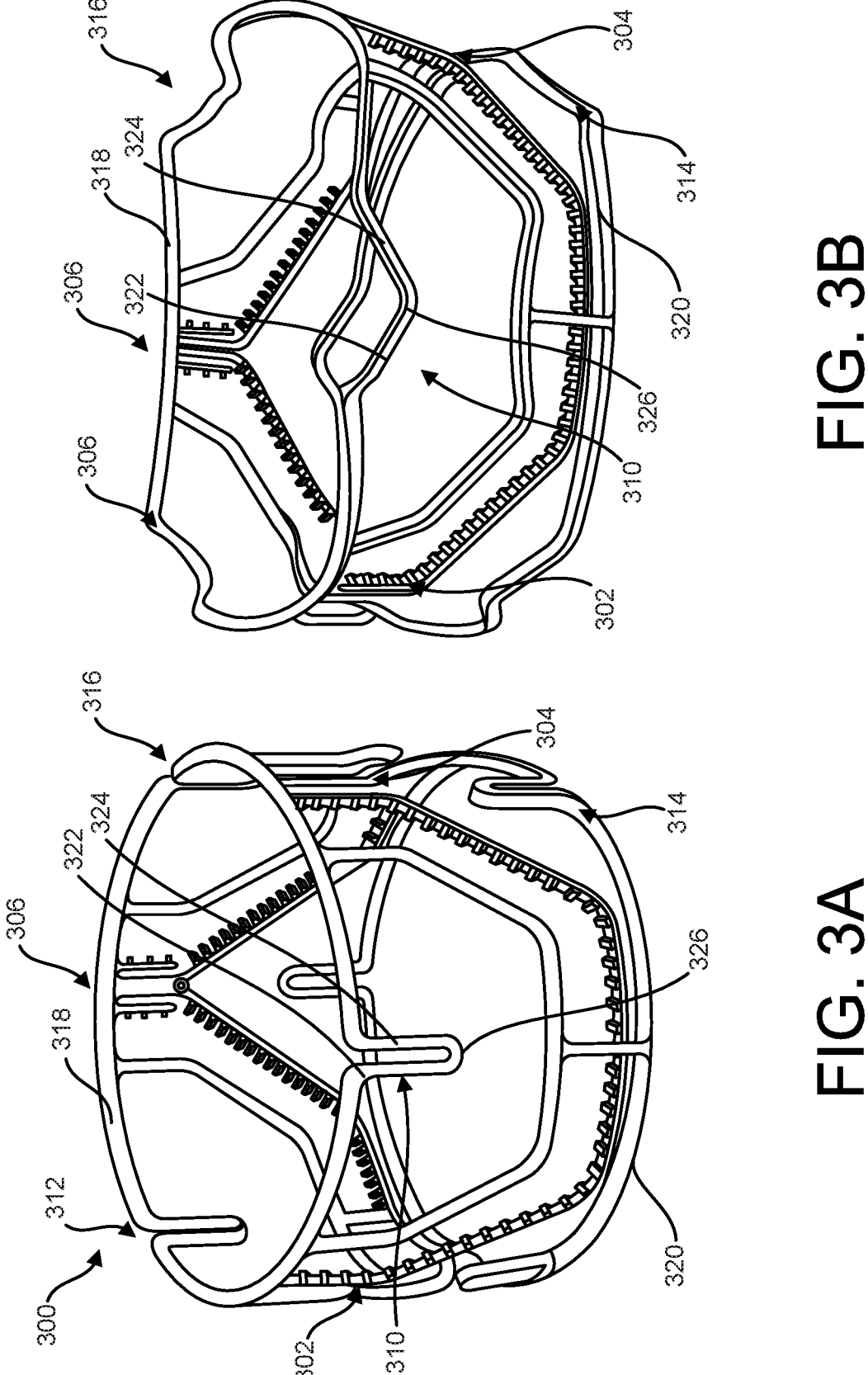
FIG. 3A is an example frame element in a first configuration, in accordance with an embodiment.
FIG. 3B is the frame element, shown in FIG. 3A, in a second configuration, in accordance with an embodiment.

FIG. 3A is an example frame element 300 in a first configuration, in accordance with an embodiment. The frame element 300 may be arranged within a conduit 102 and configured to support a valve structure 104, as shown above in FIGS. 1-2, to form a valved conduit. In other instances, the frame element 300 may be deployed within a patient without being arranged within a conduit. As shown, the frame element 300 may define an arcuate or U-shape. The frame element 300 may also include one or more commissure posts 302, 304, 306. The number of commissure posts 302, 304, 306 (or commissure regions or supports) may be equal to a number of leaflets that of the valve structure 104 that the frame element 300 is configured to support. As shown in FIG. 3A, the frame element 300 includes three commissure posts 302, 304, 306. The commissure posts 302, 304, 306 may provide locations for attachment of leaflets.

In certain instances, the frame element 300 is configured to expand to a first diameter shown in FIG. 3A in the first configuration. In this first configuration, the frame element 300 is configured to support a valve structure 104 at the first deployed diameter. The valve structure 104 and leaflets 106 (shown in FIGS. 1-2) may open and close when deployed at a target location within a patient such as replacement the pulmonary valve and a portion of the corresponding pulmonary artery.

In certain instances, the valve structure 104 and leaflets 106 (shown in FIGS. 1-2) may no longer function as desired due to growth of the patient, calcification of the leaflets 106 or other issues. As a result, the frame element 300 is configured to expand to a second, larger diameter in a second configuration (shown in FIG. 3B) in response to a force applied to an interior portion of the frame element 300. The force may be the result of a balloon to expand the frame element 300 or a delivery system carrying a replacement or second valve structure 104. The replacement or second valve structure 104 may be deployed within the expanded frame element 300.

To facilitate expansion of the frame element 300 (and conduit 102 into which the frame element 300 may be implanted), the frame element 300 may include one or more expansion elements 310, 312, 314, 316. The expansion elements 310, 312, 314, 316 may be arranged between one or more of the commissure posts 302, 304, 306 and configured to spread apart to radially expand the frame element 300 in transitioning between the first configuration and the second configuration. The frame element 300 may be configured to house a second valve structure therein in the second configuration. The frame element 300 may expand to allow for the second valve structure to be implanted and function without interference from the frame element 300.

In certain instances, the frame element 300 includes a first circular rim 318 and a second circular rim 320 connected by the commissure posts 302, 304, 306. The one or more expansion elements 310, 312, 314, 316 may form portions of one or both of the first circular rim 318 and the second circular rim 320. For ease of illustration, not all expansion elements are identified in FIGS. 3A-B. As shown, the expansion elements 310, 312, 314, 316 form portions of each of the first circular rim 318 and the second circular rim 320. In other instances, the expansion elements 310, 312, 314, 316 may form a portion of only the first circular rim 318 or only the second circular rim 320. In certain instances, the expansion elements 310, 312, 314, 316 that form portions of the second circular rim 320 may be arranged within portions of the commissure posts 302, 304, 306.

For example, the expansion element 314 is arranged within portions of the commissure post 304. The frame element 300 may include one expansion element 310, 312, 314, 316 with one of the circular rims 318, 320, one expansion element 310, 312, 314, 316 with each of the circular rims 318, 320, two expansion elements 310, 312, 314, 316 with one of the circular rims 318, 320, two expansion elements 310, 312, 314, 316 with each of the circular rims 318, 320, three expansion elements 310, 312, 314, 316 with one of the circular rims 318, 320, three expansion elements 310, 312, 314, 316 with each of the circular rims 318, 320, combinations of the above (e.g., one with one circular rim 318, and 320 and two with the other circular rim 318, 320), and additional expansion elements 310, 312, 314, 316. Thus, the frame element 300 may include a plurality of expansion elements 310, 312, 314, 316, which may be arranged between or within commissure posts 302, 304, 306.

In certain instances, the one or more expansion elements 310, 312, 314, 316 are arranged with one of the first circular rim 318 and the second circular rim 320 and extend toward the other of the first circular rim 318 and the second circular rim 320. In addition, the expansion elements 310, 312, 314, 316, as highlighted on expansion element 310 for ease of illustration, may include a first linear portion 322 and a second linear portion 324. In certain instances, the first linear portion 322 and the second linear portion 324 may be connected or coupled together by another linear portion, a jagged portion, a waved portion, a curved portion or combinations thereof.

As shown in FIG. 3A, the first linear portion 322 and the second linear portion 324 are connected by a curved portion 326. The curved portion 326 may facilitate expansion and separate the first linear portion 322 and the second linear portion 324. In addition, the curved portion 326 may absorb and distribute stress on the frame element 300 when expanding and expanded to a larger diameter. In certain instances, the first linear portion 322 and the second linear portion 324 extend substantially parallel with a longitudinal axis of the frame element 300 in the first configuration, as shown in FIG. 3A, and are configured to angle relative to the longitudinal axis of the frame element 300 in the second configuration, as shown in FIG. 3B. As shown in FIG. 3B, the frame element 300 maintains an uninterrupted or continuous outer perimeter in the second figuration. The expansion elements 310, 312, 314, 316 are configured to expand the frame element 300 without fracturing or otherwise disrupting physical integrity of the frame element 300.

As noted above, the expansion elements 310, 312, 314, 316 are configured to facilitate expansion of the frame element 300 between the first configuration, shown in FIG. 3A, and the second configuration, shown in FIG. 3B, to increase a diameter of the frame element 300. FIG. 3B shows the frame element 300, shown in FIG. 3A, in a second configuration. As shown in the second configuration, the first linear portion 322 and the second linear portion 324 transition separate and angle to allow the frame element 300 to have an expanded diameter. In addition, the expansion elements 310, 312, 314, 316 maintain integrity of the frame element 300 in the second configuration and in transitioning to the second configuration. In certain instances, the curved portion 326 may relieve forces such that the expansion elements 310, 312, 314, 316 do not fracture.

In certain instances, the frame element 300 having expansion elements 310, 312, 314, 316 on each of the first circular rim 318 and the second circular rim 320 may allow expansion of each of the first circular rim 318 and the second circular rim 320. In addition, the first circular rim 318 and the second circular rim 320 having an equal number of expansion elements 310, 312, 314, 316 may facilitate uniform expansion of the frame element 300. In addition and in certain instances, expansion elements 310, 312, 314, 316 of the first circular rim 318 may be equally spaced about the first circular rim 318 and expansion elements 310, 312, 314, 316 of the second circular rim 320 may be equally spaced about the second circular rim 320. The equal spacing may also facilitate uniform expansion of the frame element 300.

The expansion elements 310, 312, 314, 316 may be configured to hold the frame element 300 in the second configuration at the diameter intended by the interior radial force. A balloon, for example, may apply an interior force to the frame element 300 to expand the frame element 300 to a given diameter. After the balloon is no longer inflated, the expansion elements 310, 312, 314, 316 hold the frame element 300 at the given diameter. More force may expand the frame element 300 further. For example, a first force may expand the frame element 300 5%, a higher force may expand the frame element 300 10%, and an even higher force may expand the frame element 300 20% (or greater). The frame element 300 may be expanded and held by the expansion elements 310, 312, 314, 316 in a sloped manner such that the frame element 300 can be linearly or gradually expanded and maintained at a desired diameter. In certain instances, the frame element 300 may be between approximately 10 mm and approximately 20 mm in the first configuration, and expanded to approximately 20 mm to approximately 30 mm in the second configuration. The expansion elements 310, 312, 314, 316 may be configured to hold the frame element 300 at a desired diameter to facilitate housing of a desired size of a secondary valve structure that is arranged within the frame element 300 after expansion.

In certain instances, after the valved conduit that includes the frame element 300 is arranged within the patient (e.g., within the heart) and after applying a force interior to the frame element 300 to spread apart to radially expand the frame element to a second configuration having a larger diameter than the first configuration, a secondary or replacement valve structure (having leaflets and being similarly configured as the valve structure 104) may be arranged within the expanded frame element 300. The secondary or replacement valve structure may be implanted via a transcatheter approach and function as expanded within the frame element 300.

Figures 4A, 4B:
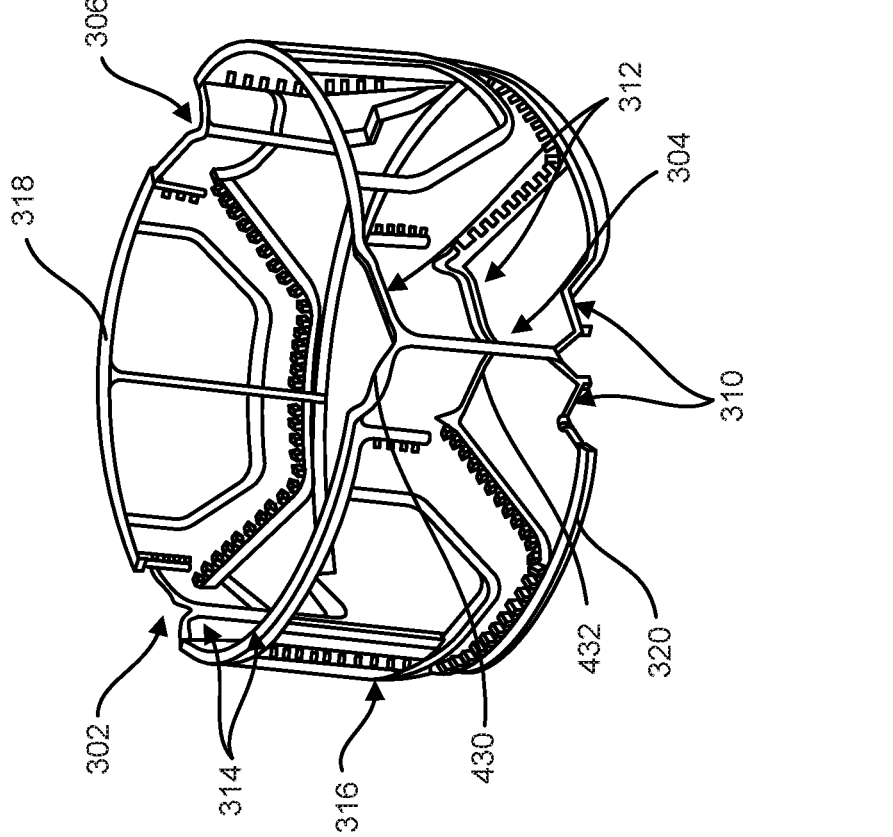
FIG. 4A is another example frame element in a first configuration, in accordance with an embodiment.
FIG. 4B is the frame element, shown in FIG. 4A, in a second configuration, in accordance with an embodiment.

FIG. 4A is another example frame element 300 in a first configuration, in accordance with an embodiment. The frame element 300 may be arranged within a conduit 102 and configured to support a valve structure 104, as shown above in FIGS. 1-2, to form a valved conduit. In other instances, the frame element 300 may be deployed within a patient without being arranged within a conduit. As shown, the frame element 300 may define an arcuate or U-shape. The frame element 300 may also include one or more commissure posts 302, 304, 306. The number of commissure posts 302, 304, 306 (or commissure regions or supports) may be equal to a number of leaflets that of the valve structure 104 that the frame element 300 is configured to support. As shown in FIG. 4A, the frame element 300 includes three commissure posts 302, 304, 306. The commissure posts 302, 304, 306 may provide locations for attachment of leaflets. In certain instances, the frame element 300 includes a first circular rim 318 and a second circular rim 320 connected by the commissure posts 302, 304, 306.

In certain instances, the frame element 300 is configured to expand to a first diameter shown in FIG. 4A in the first configuration. In this first configuration, the frame element 300 is configured to support a valve structure 104 at the first deployed diameter. The valve structure 104 and leaflets 106 (shown in FIGS. 1-2) may open and close when deployed at a target location within a patient such as replacement the pulmonary valve and a portion of the corresponding pulmonary artery.

In certain instances, the valve structure 104 and leaflets 106 (shown in FIGS. 1-2) may no longer function as desired due to growth of the patient, calcification of the leaflets 106 or other issues. As a result, the frame element 300 is configured to expand to a second, larger diameter in a second configuration (shown in FIG. 4B) in response to a force applied to an interior portion of the frame element 300. The force may be the result of a balloon to expand the frame element 300 or a delivery system carrying a replacement or second valve structure 104. The replacement or second valve structure 104 may be deployed within the expanded frame element 300.

To facilitate expansion of the frame element 300 (and conduit 102 into which the frame element 300 may be implanted), the frame element 300 may include one or more expansion elements 310, 312, 314, 316. For ease of illustration, not all expansion elements are identified in FIGS. 4A-B. The expansion elements 310, 312, 314, 316 may be arranged adjacent to one or more of the commissure posts 302, 304, 306 and configured to spread apart to radially expand the frame element 300 in transitioning between the first configuration and the second configuration. As shown, the expansion elements 310, 312, 314, 316 are arranged at upper and lower portions of the commissure posts 302, 304, 306. In certain instances, each of the commissure posts 302, 304, 306 includes upper and lower expansion elements 310, 312, 314, 316, and in other instances, one or more of the commissure posts 302, 304, 306 includes upper and lower expansion elements 310, 312, 314, 316. Further, one or more of the commissure posts 302, 304, 306 may include only one of an upper and lower expansion element 310, 312, 314, 316.

Upper expansion elements 312, 314 may include a first portion 430 and a second portion 432. Each of the first portion 430 and the second portion 432 of the upper expansion elements 312, 314 include arms on either side of an adjacent one of the commissure posts 302, 304, 306. As shown in FIG. 4B, the arms of the first portion 430 and the second portion 432 of the upper expansion elements 312, 314 separate from the adjacent one of the commissure posts 302, 304, 306 in the second (expanded) configuration. The lower expansion elements 310, 316 may include accordion-like portions that are collapsed toward an adjacent one of the commissure posts 302, 304, 306 in the first configuration. In the second configuration, as shown in FIG. 4B, the lower expansion elements 310, 316 expand outwardly relative to the adjacent one of the commissure posts 302, 304, 306. The accordion-like portions may include curved transitions between the linear shapes. In addition and as shown in FIG. 2, either or both of the upper and lower expansion elements 310, 312, 314, 316 may include triangular shapes or other curved shapes to facilitate expansion. As shown in FIG. 4B, the frame element 300 maintains an uninterrupted or continuous outer perimeter in the second figuration. The expansion elements 310, 312, 314, 316 are configured to expand the frame element 300 without fracturing or otherwise disrupting physical integrity of the frame element 300.

The frame element 300 having upper and lower expansion elements 310, 312, 314, 316 may isolate deformation of the frame element 300 to between the commissure posts 302, 304, 306. As a result, the frame element 300 is configured to deform to maintain the gaps (as shown in FIG. 1B) between the leaflets. The upper and lower expansion elements 310, 312, 314, 316 may be configured to hold the frame element 300 in the second configuration at the diameter intended by the interior radial force. The frame element 300 may be expanded and held by the upper and lower expansion elements 310, 312, 314, 316 in a sloped manner such that the frame element 300 can be linearly or gradually expanded and maintained at a desired diameter.

In certain instances, after the valved conduit that includes the frame element 300 is arranged within the patient (e.g., within the heart) and after applying a force interior to the frame element 300 to spread apart to radially expand the frame element to a second configuration having a larger diameter than the first configuration, a secondary or replacement valve structure (having leaflets and being similarly configured as the valve structure 104) may be arranged within the expanded frame element 300. The secondary or replacement valve structure may be implanted via a transcatheter approach and function as expanded within the frame element 300.

The frame elements discussed herein may be formed from other materials such as stainless steel, L605 steel, polymers, MP35N steel, polymeric materials, Pyhnox, Elgiloy, or any other appropriate biocompatible material, and combinations thereof, can be used as the material of the frames. In other instances, the frame elements may be formed from Nitinol (NiTi)

The conduits discussed herein may be a synthetic conduit with at least one flexible synthetic valve leaflet attached to the synthetic conduit. Prior to implantation, the synthetic valve leaflet and/or the synthetic conduit that may be rinsed in saline and does not require pre-clotting. Subsequently, the synthetic valve leaflet and the synthetic conduit may be surgically implanted. The synthetic valve leaflet and the synthetic conduit may be a replacement of the native pulmonary valve or of a previously implanted pulmonary valved conduit where partial or complete reconstruction of the right ventricular outflow tract and/or main pulmonary artery is desired. In certain instances, installation of the synthetic valve leaflet and the synthetic conduit includes identifying the inflow and outflow regions (or ends) of the conduit, accessing the intended position with respect to the coronary arteries to assure there is no risk of coronary compression when implanted, and optionally trimming the inflow end and or outflow end of the conduit, while under moderate tension, to the appropriate length for implantation.

The valved conduit discussed herein are used to replace diseased anatomy in a surgical operation. Prior to implantation, the valved conduit may be rinsed in saline and does not require pre-clotting. In accordance with one method of treatment, the valved conduit is used as a replacement for an aortic valve and a portion of the ascending aorta, such as in an aortic root replacement. Implanting the valved conduit includes identifying the inflow and outflow portions of the conduit, accessing the intended position with respect to the anatomy, and optionally trimming the inflow end or portion and or outflow end or portion of the conduit, while under moderate tension, to the appropriate length for implantation. The ascending aorta is sectioned and the inflow portion and/or inflow end of the valved conduit is sutured or otherwise coupled to the left ventricle adjacent to or in the place of an excised aortic valve. The outflow portion and/or the outflow end of the valved conduit is sutured to the sectioned ascending aorta. Coronary arteries are allowed to remain on the ascending aorta or they may be sutured to the outflow portion of the conduit and a flow path is provided from the conduit lumen to the coronary arteries.

In accordance with another method of treating aortic valve disease by replacing the aortic root of a patient, the method comprises the steps of providing a valved conduit in accordance with embodiments herein and surgically implanting the valved conduit. The method may further comprise identifying an inflow portion (or end) and outflow portion (or end) of the conduit; accessing the intended position with respect to anatomy; optionally trimming the inflow portion (or end) and outflow portion (or end) of the conduit to the appropriate length for implantation; optionally outwardly tapering the inflow end or optionally everting and rolling the inflow portion toward the leaflet structure to define a sewing cuff; sectioning the ascending aorta; coupling the inflow portion of the valved conduit to the left ventricle adjacent to or in the place of an excised aortic valve; and coupling the outflow portion of the valved conduit to the sectioned ascending aorta. The method may further comprise coupling coronary arteries to the outflow portion of the conduit; and establishing a flow path from the conduit lumen to the coronary arteries.

In certain embodiments, the conduits discussed herein include an expanded fluoropolymer material made from porous ePTFE membrane.

The expandable fluoropolymer, used to form the expanded fluoropolymer material described, can comprise PTFE homopolymer. In alternative embodiments, blends of PTFE, expandable modified PTFE and/or expanded copolymers of PTFE can be used.

The expanded fluoropolymer membrane can comprise any suitable microstructure, such as pores, for achieving the desired leaflet performance. Other biocompatible polymers which can be suitable for use in leaflet include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

In various examples, any of the leaflet constructs described herein (e.g., leaflet construct) may be formed of a biocompatible, synthetic material (e.g., including ePTFE and ePTFE composites, or other materials as desired). Other biocompatible polymers which can be suitable for use in synthetic leaflets include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

In other examples, such leaflet construct is formed of a natural material, such as repurposed tissue, including bovine tissue, porcine tissue, or the like.

As used herein, the term "elastomer" refers to a polymer or a mixture of polymers that has the ability to be stretched to at least 1.3 times its original length and to retract rapidly to approximately its original length when released. The term "elastomeric material" refers to a polymer or a mixture of polymers that displays stretch and recovery properties similar to an elastomer, although not necessarily to the same degree of stretch and/or recovery. The term "non-elastomeric material" refers to a polymer or a mixture of polymers that displays stretch and recovery properties not similar to either an elastomer or elastomeric material, that is, considered not an elastomer or elastomeric material.

In accordance with some embodiments herein, the leaflet construct comprises a composite material having at least one porous synthetic polymer membrane layer having a plurality of pores and/or spaces and an elastomer and/or an elastomeric material and/or a non-elastomeric material filling the pores and/or spaces of the at least one synthetic polymer membrane layer. In accordance with other examples, the leaflet construct further comprises a layer of an elastomer and/or an elastomeric material and/or a non-elastomeric material on the composite material. In accordance with some examples, the composite material comprises porous synthetic polymer membrane by weight in a range of about 10% to 90%

An example of a porous synthetic polymer membrane includes expanded fluoropolymer membrane having a node and fibril structure defining the pores and/or spaces. In some examples, the expanded fluoropolymer membrane is expanded polytetrafluoroethylene (ePTFE) membrane. Another example of porous synthetic polymer membrane includes microporous polyethylene membrane.

Examples of an elastomer and/or an elastomeric material and/or a non-elastomeric material include, but are not limited to, copolymers of tetrafluoroethylene and perfluoromethyl vinyl ether (TFE/PMVE copolymer), (per)fluoroalkyl-vinylethers (PAVE), urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing. In some examples, the TFE/PMVE copolymer is an elastomer comprising essentially of between and including 60 and 20 weight percent tetrafluoroethylene and respectively between and including 40 and 80 weight percent perfluoromethyl vinyl ether. In some examples, the TFE/PMVE copolymer is an elastomeric material comprising essentially of between and including 67 and 61 weight percent tetrafluoroethylene and respectively between and including 33 and 39 weight percent perfluoromethyl vinyl ether. In some examples, the TFE/PMVE copolymer is a non-elastomeric material comprising essentially of between and including 73 and 68 weight percent tetrafluoroethylene and respectively between and including 27 and 32 weight percent perfluoromethyl vinyl ether. The TFE and PMVE components of the TFE-PMVE copolymer are presented in wt %. For reference, the wt % of PMVE of 40, 33-39, and 27-32 corresponds to a mol % of 29, 23-28, and 18-22, respectively.

In some examples, the TFE-PMVE copolymer exhibits elastomer, elastomeric, and/or non-elastomeric properties.

In some examples, the composite material further comprises a layer or coating of TFE-PMVE copolymer comprising from 73 to 68 weight percent tetrafluoroethylene and respectively from 27 to 32 weight percent perfluoromethyl vinyl ether.

In some examples, the leaflet construct is an expanded polytetrafluoroethylene (ePTFE) membrane having been imbibed with TFE-PMVE copolymer comprising from 60 to 20 weight percent tetrafluoroethylene and respectively from 40 to 80 weight percent perfluoromethyl vinyl ether, the leaflet construct further including a coating of TFE-PMVE copolymer comprising from 73 to 68 weight percent tetrafluoroethylene and respectively 27 to 32 weight percent perfluoromethyl vinyl ether on the blood-contacting surfaces.

As discussed above, the elastomer and/or an elastomeric material and/or a non-elastomeric material may be combined with the expanded fluoropolymer membrane such that the elastomer and/or the elastomeric material and/or the non-elastomeric material occupies substantially all of the void space or pores within the expanded fluoropolymer membrane.

In accordance with an embodiment, the composite material can include an expanded fluoropolymer material made from porous ePTFE membrane.

The expanded fluoropolymer membrane, used to form some of the composites described, can comprise PTFE homopolymer. In alternative embodiments, blends of PTFE, expandable modified PTFE and/or expanded copolymers of PTFE can be used.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A valved conduit comprising:
   a conduit having an interior surface and an exterior surface;
   a frame element arranged within the conduit and having commissure posts arranged about the frame element, the frame element having a first diameter in a first configuration and configured to support a valve structure having leaflets configured to open to permit flow and close to occlude a conduit lumen and prevent flow in response to differential fluid pressure and to expand to a second, larger diameter in a second configuration in response to a force applied to an interior portion of the frame element; and one or more expansion elements arranged between or adjacent to the commissure posts and configured to spread apart to radially expand the frame element in transitioning from the first configuration to the second configuration;

wherein the frame element includes a first circular rim and a second circular rim connected by the commissure posts; and wherein the one or more expansion elements are one or more first expansion elements forming portions of the first circular rim and the valved conduit further includes one or more second expansion elements forming portions of the second circular rim.

2. The valved conduit of claim 1, wherein the frame element is configured to house a second valve structure therein in the second configuration.

3. The valved conduit of claim 1, wherein the one or more first expansion elements extend toward the second circular rim.

4. The valved conduit of claim 3, wherein the one or more first expansion elements each include a first linear portion, a second linear portion, and a curved portion.

5. The valved conduit of claim 4, wherein the first linear portion and the second linear portion extend substantially parallel with a longitudinal axis of the frame element in the first configuration and are configured to angle relative to the longitudinal axis of the frame element in the second configuration.

6. The valved conduit of claim 5, wherein the one or more first expansion elements are arranged between the commissure posts.

7. The valved conduit of claim 5, wherein the one or more first expansion elements are arranged adjacent to the commissure posts.

8. The valved conduit of claim 5, wherein the one or more first expansion elements are arranged between portions of the commissure posts.

9. The valved conduit of claim 5, wherein the one or more first expansion elements includes a plurality of first expansion elements arranged between portions of each of the commissure posts.

10. The valved conduit of claim 1, wherein the one or more first expansion elements and the one or more second expansion elements are configured to increase a diameter of the frame element.

11. A valved conduit for housing a first valve structure and allowing expansion for housing a second valve structure, the valved conduit comprising:

a conduit having an interior surface and an exterior surface; and a frame element arranged within the conduit including a first diameter in a first configuration and configured to support the first valve structure having leaflets configured to open to permit flow and close to occlude a conduit lumen and prevent flow in response to differential fluid pressure, the frame element having:

a first circular rim, a second circular rim, commissure posts arranged about the frame element and connecting the first circular rim and the second circular rim, one or more first expansion elements arranged between or adjacent to the commissure posts along the first circular rim, and one or more second expansion elements arranged between or adjacent to the commissure posts along the second circular rim, wherein the one or more first expansion elements and the one or more second expansion elements are configured to spread apart to radially expand the frame element in transitioning between the first configuration and a second, larger diameter in a second configuration to support the second valve structure having leaflets in response to a force applied to an interior portion of the frame element.

12. The valved conduit of claim 11, wherein the frame element is configured to deform to maintain gaps between the leaflets of the second valve structure.

13. The valved conduit of claim 11, wherein the one or more first expansion elements and the one or more second expansion elements are configured to hold the frame element in the second configuration at the second diameter.

14. The valved conduit of claim 11, wherein the one or more first expansion elements and the one or more second expansion elements are configured to expand in a sloped manner to radially expand the frame element.

* * * * *